United States Patent [19]

Chagnon et al.

[11] Patent Number: 5,547,682
[45] Date of Patent: Aug. 20, 1996

[54] PREPARATION AND USE OF NOVEL INJECTABLE RES AVOIDING INORGANIC PARTICLES FOR MEDICAL APPLICATION

[75] Inventors: Mark S. Chagnon, Pelham, N.H.; Stephen E. Burkle, Andover, Mass.; Michelle J. Carter, Derry; Tracy J. Hamilton, Plaistow, both of N.H.; John Havelick, Jr., Wakefield, Mass.; Deborah A. Kaplan, Derry, N.H.; Kristin L. Marzloff, Auburn, N.H.

[73] Assignee: BioQuest, Incorporated, Atkinson, N.H.

[21] Appl. No.: 277,655

[22] Filed: Jul. 20, 1994

Related U.S. Application Data

[63] Continuation-in-part of Ser. No. 894,260, Jun. 8, 1992, which is a continuation-in-part of Ser. No. 556,169, Jul. 23, 1990, abandoned, which is a continuation-in-part of Ser. No. 455,071, Dec. 22, 1989, abandoned.

[51] Int. Cl.⁶ .............................. A61K 9/16; A61K 9/50
[52] U.S. Cl. .......................... 424/497; 424/9.1; 424/9.3
[58] Field of Search .................... 424/497, 9.3, 9.1; 514/836

[56] References Cited

U.S. PATENT DOCUMENTS

| | | | |
|---|---|---|---|
| 4,018,886 | 4/1977 | Giaever | 424/12 |
| 4,048,481 | 9/1977 | Bailey, Jr. et al. | 235/153 AK |
| 4,247,406 | 1/1981 | Widder et al. | 252/62.53 |
| 4,421,660 | 12/1983 | Solc Nee Hajna | 252/62.54 |
| 4,552,812 | 11/1985 | Margel et al. | 428/407 |
| 4,624,846 | 11/1986 | Goldenberg | 424/1.1 |
| 4,624,923 | 11/1986 | Margel | 435/176 |
| 4,637,929 | 1/1987 | Quay | 424/9 |
| 4,654,267 | 3/1987 | Ugelstad et al. | 428/407 |
| 4,675,173 | 6/1987 | Widder | 424/9 |
| 4,721,914 | 1/1988 | Fukushima et al. | 324/320 |
| 4,731,239 | 3/1988 | Gordon | 424/9 |
| 4,732,811 | 3/1988 | Margel | 428/403 |
| 4,735,796 | 4/1988 | Gordon | 424/9 |
| 4,758,429 | 7/1988 | Gordon | 424/85 |
| 4,783,336 | 11/1988 | Margel et al. | 424/462 |
| 4,813,399 | 3/1989 | Gordon | 600/12 |
| 4,861,705 | 8/1989 | Margel | 435/2 |
| 4,895,650 | 1/1990 | Wang | 210/222 |
| 4,915,933 | 4/1990 | Matwiyoff | 424/9 |
| 4,999,445 | 3/1991 | White et al. | 556/138 |
| 5,068,098 | 11/1991 | Schweighardt et al. | 424/9 |
| 5,071,076 | 12/1991 | Chagnon et al. | 241/21 |
| 5,077,037 | 12/1991 | Wallace | 424/9 |
| 5,091,206 | 2/1992 | Wang et al. | 427/2 |
| 5,141,740 | 8/1992 | Rajagopalan et al. | 424/9 |
| 5,154,914 | 10/1992 | Elgavish et al. | 424/9 |
| 5,158,871 | 10/1992 | Rossomando et al. | 435/7.32 |
| 5,160,725 | 11/1992 | Pilgrimm | 424/9 |
| 5,162,109 | 11/1992 | Rajagopalan | 424/1.1 |
| 5,198,208 | 3/1993 | Berg et al. | 424/1.1 |
| 5,217,706 | 6/1993 | Rajagopalan et al. | 424/9 |
| 5,221,485 | 6/1993 | Bosworth et al. | 210/651 |
| 5,242,683 | 9/1993 | Klaveness | 424/9 |
| 5,246,696 | 9/1993 | Dean | 424/9 |
| 5,283,079 | 2/1994 | Wang et al. | 427/2 |
| 5,284,647 | 2/1994 | Niedballa et al. | 424/81 |
| 5,290,537 | 3/1994 | Moore et al. | 424/9 |
| 5,314,680 | 5/1994 | Rajagopalan et al. | 424/9 |
| 5,320,826 | 6/1994 | Unger | 424/9 |
| 5,322,682 | 6/1994 | Bartzokis et al. | 424/9 |
| 5,328,861 | 7/1994 | Miyakawa | 437/40 |

*Primary Examiner*—Thurman K. Page
*Assistant Examiner*—William E. Benston, Jr.
*Attorney, Agent, or Firm*—Hayes, Soloway, Hennessey, Grossman & Hage, P.C.

[57] ABSTRACT

Novel N-RES agents for use in vitro and in vivo medical and biological applications, such as, for example MRI and/or intravenous administration of pharmaceutical agents are described. The novel N-RES agents are prepared by coating inorganic core particles with a poly(acrylic acid)—poly-(alkylene ether) graft copolymer. The resulting polymer-coated inorganic particle cores are useful as imaging agents, therapeutic agents or carriers having increased circulation time due to decrease uptake or recognition by the RES.

13 Claims, 8 Drawing Sheets

PREPARATION AND USE OF NOVEL INJECTABLE RES AVOIDING INORGANIC PARTICLES FOR MEDICAL APPLICATION

This application is a continuation-in-part of co-pending application Ser. No. 07/894,260 filed Jun. 8, 1992, which is a continuation-in-part of U.S. application Ser. No. 07/556,169, filed Jul. 23, 1990 now abandoned, which is a continuation-in-part of U.S. application Ser. No. 07/455,071, filed Dec. 22, 1989, now abandoned.

RELATED APPLICATIONS

Applications, 07/706,478, filed Dec. 13, 1991 now abandoned, and 07/565,801, now U.S. Pat. No. 5,071,076, are incorporated by reference.

FIELD OF THE INVENTION

This invention relates to the preparation of novel coated inorganic particles and the use thereof. The coated inorganic particles of the present invention have particular utility for use as contrast agents in connection with the imaging of discrete areas of the body and will be described in connection with such utility, although other utilities are contemplated.

BACKGROUND OF THE INVENTION

MR imaging of the human body can display both normal anatomy and a variety of organ pathologies, including tumors. For example, the liver, pancreas, spleen and gall bladder can be imaged by tomographic slices in various planes. The techniques used for MRI liver examination have included delineation by spinecho, inversion recovery, and saturation recovery pulse sequences, but definition of normal from abnormal has not been predictable. In hepatic MRI, specifically, contrast resolution of the hepatic images varies greatly depending on the data acquisition technique employed to obtain the image although tumors associated with the liver or spleen usually result in prolongation of both the longitudinal (T1) and the transverse (T2) relaxation times as compared with normal tissues. Earlier reports have emphasized the importance of using paramagnetic agents to increase the T1 differences between normal and pathologic tissues and considered coincidental T2 diminution an impediment.

Paramagnetic contrast agents as free metal ions, chelates, or insoluble metal compounds have been described for use in enhancing intrinsic contrast in MR imaging. Such paramagnetic metals include gadolinium, chromium, copper, manganese and iron. Because of possible toxicity, soluble chelates have been suggested for parenteral administration and insolubilized compounds for oral administration. Heretofore, however, the targeting of stable contrast agents to the liver and spleen has not been satisfactory.

Effective, safe reticuloendothelial system (RES) MRI contrast agent which can increase the sensitivity and differentiation of normal and pathologic tissue in the liver or spleen have been proposed in the art. However, existing modalities for other imaging procedures for the liver and spleen have approximately a 10-20% false-negative rate for detecting hepatic metastases, and a 40-50% false-negative rate for detecting lymphomatous involvement, necessitating laproscopic staging. Further, as pointed out above, tumor involvement of liver, spleen and other tissues has consistently been shown to increase T1 and T2 relaxation parameters to a variable and unpredictable degree, which also results in a high incidence of false-negative. RES agents are useful because liver replaced by tumor does not possess RES cells and therefore does not take up the contrast agent. Non-RES agents more randomly distribute between normal and pathologic tissue.

Hepatic disease conditions resulting in abnormally high levels of iron in the liver have been shown to produce laterations of tissue relaxation times as observed by MRI. See, for example, Doyle et al., *AM J. Roentgenol* (1982) 138: 193-200; Stark et al, *Radiology* (1983) 148: 743-751; and Runge, et al., *Am. J. Roentgenol* (1983) 141: 943-948. Observed decreases in T1 have been attributed either to paramagnetic enhancement of longitudinal relaxation, or to alterations of hydrated tissue proteins. Heretofore, the production of T2 diminution as seen in these disease states has not been produced with a potent, safe contrast agent. Soluble iron compounds have been tested as MRI contrast agents. Wesbey, et al *Radiology* (1983) 149: 175-180.

The foregoing discussion is taken largely from Widder U.S. Pat. No. 4,675,173 who proposed MRI examination employing encapsulated paramagnetic contrast agents. According to Widder the contrast agents preferably are ferromagnetic as well as paramagnetic. By utilizing microspheres within the size range of 1.5 to 8 microns, such as 3 to 5 microns the parenterally administered contrast agents reportedly are rapidly segregated by the reticuloendothelial system and concentrated in the liver and spleen. Effective segregation and concentration in these organs is said to occur in as short a time as 1 to 10 minutes, and only a small quantity of the microspheres reportedly needs to be administered for effective reduction of the T2 relaxation time of the subject's liver and/or spleen. Actually, by the early 1960's, the first stable magnetic fluid colloid had been described. Later research led to the development of a separations device based on magnetic density gradients in magnetic fluid columns. By 1979, magnetic particles coated with appropriate functional chemical grounds for affinity chromatography separations were reported.

For example, dextran/magnetite has been explored (see Hasegawa et al, U.S. Pat. No. 4,101,435; Molday, U.S. Pat. No. 4,454,773, and Schroder, U.S. Pat. No. 4,501,726). The complexes of dextran and iron oxide have had some success, but all have high molecular weight coatings (at least 500,000) which reportedly lead to adverse reactions in clinical trials. Apparently, such high molecular weight coatings dissociate, leaving the metal oxide free to aggregate.

Similarly, in 1985 Nycomed disclosed their efforts (e.g. PCT appln. WO85/02772) towards the development of particles for contrast agent applications. It was reported that it was best to fully enclose magnetic particles in a matrix which is "biocompatible", and that matrix materials included carbohydrates, polyamino acids (albumin) and certain synthetic polymers (acrylates, polystyrene, etc.).

Chan et al report preparing compounds known as "Ferrosomes". *Invest. Radiol.* 27(6), pp. 443-49 (1992). These are lipid-coated iron oxide particles and such particles were used as contrast agents. In a similar manner, Eli Lilly has reported on drug carrier formulations (U.S. Pat. No. 4,331,654) consisting of magnetically localizable, biodegradable, lipid microspheres.

The first commercial application of magnetic separations was described by Chagnon et al in U.S. Pat. No. 4,268,037. The Chagnon patent describes the use of amine terminated silane coupled magnetic particles for immunodiagnostic applications. The materials described in the Chagnon et al patent are now used commercially in medical diagnostic kits.

Magnetic separations have not been exclusively applied to in vitro applications. The use of magnetic separations for in vivo applications is becoming increasingly more accepted and important as a therapeutic and diagnostic tool. By the early 1980's published reports described the magnetic targeting and isolation of chemotherapeutic drugs into rat-tail sarcoma. Widder (U.S. Pat. Nos. 4,849,210; 4,247,406; and 4,230,685) described the use of magnetic albumin spheres for ultrasound contrast media and magnetic drug targeting. See also Widder U.S. Pat. Nos. 4,357,259; 4,345,588; and 5,179,955. And, Schroder (U.S. Pat. No. 4,501,726) reports a method of preparing magnetic starch beads for use in MRI imaging for the separation of T1/T2 relaxation signals. See also U.S. Pat. Nos. 4,770,183; 4,827,945 and 4,331,654.

Liposomes have received a great deal of attention over the past due to their ability to carry large amounts of therapeutic agents with decreased toxicity (Mayer, L. D., Bally, M. B., Loughrey, H., Masin, D., Cullins, P. R. (1990) *Cancer Research* 50, 575–579, Lopez-Berstein, G., Fidler, I. J., Liss (1989), New York pp 353–365 Juliano; A. L. Stamp D. (1978) "Pharmacokinetics of Liposomes-Encapsulated Antitumor Drugs," *Biochem Pharmacal* 28, 21–27), and recently as a protective delivery system of oligonucleotides (Thierry, A., Rahman, A. Dritschilo, A., "Liposomal Delivery As a New Approach to Transport Antisense Oligonucleotides" *Gene Regulation: Biology of Antisense RNA and DNA*, Raven Press N.Y. (1992). Lipid vesicle are formed around the drug of choice and the material is transported through the blood stream to an endothelial barrier. Crude targeting, done by size mediation, and chemical targeting done by using liposomes with antibodies on their surface, have been studied (Hughs, B., Kennel, S., Lee R., Huang, L., (1989) Monoclonal Antibody Targeting of Liposomes to Mouse Lung", *In Vivo Cancer Research* 49, 6214–6220 (1989) The liposome binds to the endothelial target, the drug is released from the liposome, transcytosed across the membrane and delivered to the tissue. This approach has suffered from the following three shortcomings: Liposomes have difficulty crossing the endothelium intact with the drug. The drug is therefore subject to entrapment in the basement membrane and lysosomal degradation after release from the liposome. Liposomes are not sheer stable, and the size discrimination targeting is inhibited by liposome instability in the bloodstream. Finally, attempts to target liposomes using antibodies have resulted in the only limited success (Papahakjopoulos, D., Gabizon, A., "Targeting of Liposomes to Tumor Cells" *In Vivo Ann, N.Y., Acad. Sci.* 507:64–74(87).

Several novel nanoparticle systems have been explored for a variety of purposes over the past several years. Microporous polymer beads that are less than 100 nm in diameter have been demonstrated to be effective in evading capture by the RES. Systems have been designed using these porous polymer vehicles loaded with a drug to slowly release nanoparticles and controlled dosages of drugs into the blood over a long period of time (Ruxandra, G., Minamitake, Y. Peachia, M., Trubetsky, V. Langer, "Biodegradable Long-Circulating Polymeric Nanospheres", *Science* Vol. 263, (1994). Iron oxide that has the ability to target hepatocytes has also been evaluated for MR imaging. (Josephson, L., Groman, E. Menz, E., Lewis, J., and Bengele, H. "A Functionalized Superparamagnetic Iron Oxide Colloid as a Receptor Directed MR Contrast Agent, *Magn. Reson. Imag.* 8,637–646, (1990); Reimer, P., Weissleder, R., Lee, A., Wittenberg, J., Brady, T., "Receptor Imaging: Application to MR Imaging of Liver Cancer," *Radiology* 177:729–734 (1990); Weissleder, R., Lee, A., Khous, B., Shen, T., Brady, T., "Antimyosin-l Labeled Monocrystalline Iron Oxide Allows Detection of Myocardial Infarct", *Radiology* 182,381–385 (1992).

The ideal drug delivery system is one that can transport a therapeutic agent, avoid capture by the RES, be targeted to a specific cell population, concentrate therapeutic levels of the drug at the site and be capable of releasing the drug to the targeted area in a controlled fashion. The clinical goal is to increase the therapeutic index of the drug by decreasing its systemic dosage while increasing the locally effective dosage by concentrating the agent at the site where it is needed. This strategy, designed to increase the desired effects and to decrease side effects of many drugs, may make it possible to utilize therapeutically beneficial molecules that currently can not be used because of the toxic effects that they cause when administered systematically.

In all of this previous work, the use of magnetic particles as contrast agents for magnetic resonance imaging (MRI) has been limited to the organs of the RES due to its rapid blood clearance. However, an advantage in enhanced separations, for example, could be achieved if the magnetic particles could be altered to avoid particular uptake by the RES. Solid particles have the advantages of having sheer resistant size, a controllable shape, carrying a predictable and stable surface charge and maintaining a uniform stable size distribution both in vitro and in vivo. Inorganic particle cores are of particular interest because of their biodegradability. Particles of sufficiently small diameter with hydrophilic surfaces that evade RES uptake have been synthesized and studied (Chagnon, M., Carter, M., Ferris, J., Gray, M., Hamilton, Tr., Rudd, E., "Preparation of Controlled Size Inorganic Particles For Use In Separations, As Magnetic Molecular Switches, As An Inorganic Lipsomes for Medical Applications," International Publication Number WO 93/26019 (1993).

Iron oxide particles with a significant decrease in RES recognition and an increase in blood circulation time would therefore be extremely beneficial. Reducing recognition by the RES would result in an increased circulation time for particulates which would permit development of an MRI agent for perfusion. By coupling specific targeting chemistries, the resulting material also could be used for imaging discrete areas of the body such as tumors and/or for targeting drug delivery.

OBJECTS OF THE INVENTION

It is a primary object of the invention to provide a novel RES avoiding coating for inorganic particles used for immuno diagnostic and therapeutic applications. It is also a primary object of the invention to provide a new and improved inorganic particle imaging agent which overcomes the aforesaid and other disadvantages of the prior art.

A more specific object of the invention is to provide a method for producing RES evading (N-RES) inorganic particle agents for use as in vivo medical biological agents.

SUMMARY OF THE INVENTION

The present invention provides novel N-RES agents for use in vitro and in vivo medical and biological applications, such as, for example, MRI and/or intravenous administration of pharmaceutical agents. The novel N-RES agents are prepared by coating inorganic core particles (e.g. metals, metal alloys, metal salts, metal organic particles, metal oxides, metal hydroxides, and mixed lattices thereof) with a poly(acrylic acid)—poly(alkylene ether) graft polymer of a structure having the following formula:

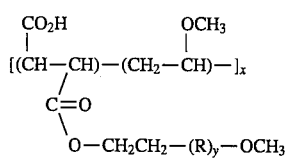

wherein R is preferably an aklylene ether of $C_1$-$C_6$ (e.g. methylene oxide, ethylene oxide, isopropylene oxide, butylene oxide, isobutylene oxide, or copolymers thereof), x is a whole number of at least 1, and y is a whole number of at least 1. The resulting polymer-coated inorganic particle cores are useful as imaging agents, therapeutic agents or carriers having increased circulation time due to decreased uptake or recognition by the RES.

The overall process is as follows: First, inorganic core particles are prepared at a suitable, controlled size, for the desired use, e.g. using any conventional inorganic core particle preparation method for injection, and the particles are then coated with the graft polymer coating. In a preferred embodiment of the invention, controlled size inorganic core particles are prepared by contacting an aqueous solution of an inorganic salt in an inorganic base across a porous membrane wherein the membrane contains a plurality of pores which allows the precipitation of substantially monodispersed size inorganic oxide particles on one side of the membrane and precipitation of a salt of the corresponding base on a second side of the membrane, following the teachings of my aforesaid co-pending U.S. patent application Ser. No. 07/894,206. Alternatively, the inorganic cores can be prepared by the reaction of metallocenes with aqueous metal hydroxide slurries followed by milling to desired particle size following the teachings of my U.S. Pat. No. 5,071,076. In a third embodiment, the core particles are prepared by the direct precipitation of iron oxide from a dilute solution of $Fe^{+2}$ and $Fe^{+3}$ with a large excess of Base (RGI).

The N-RES particle agents of the present invention are then prepared by coating the inorganic core particles with a poly (acrylic acid)—poly (alkylene ether) graft copolymer to produce an agent which can be used for MRI imaging applications, or to transport a therapeutic agent, while avoiding capture by the RES.

The invention will be further described in connection with the following detailed description and drawings wherein.

Figure 3:
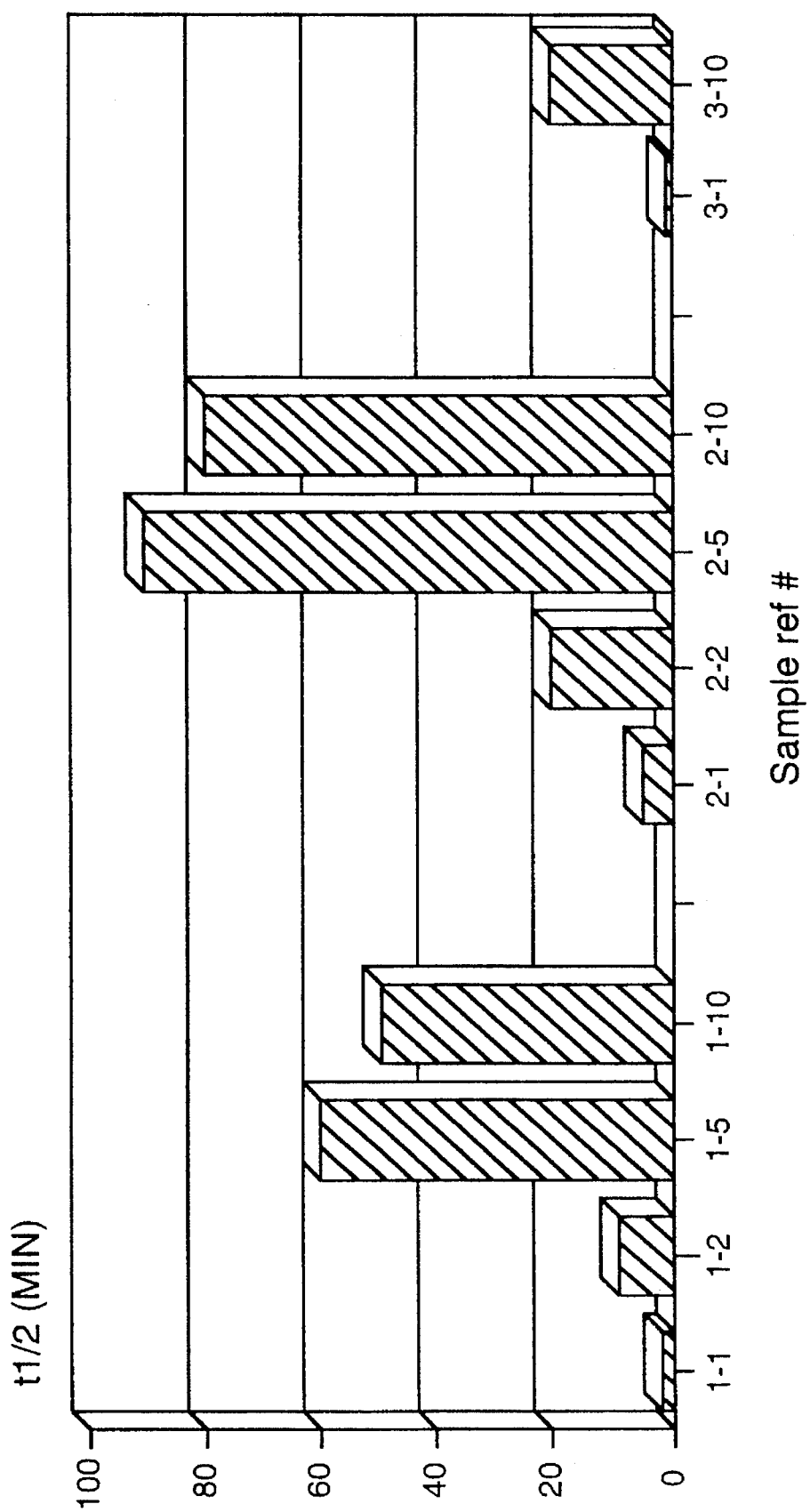
Figure 4A:
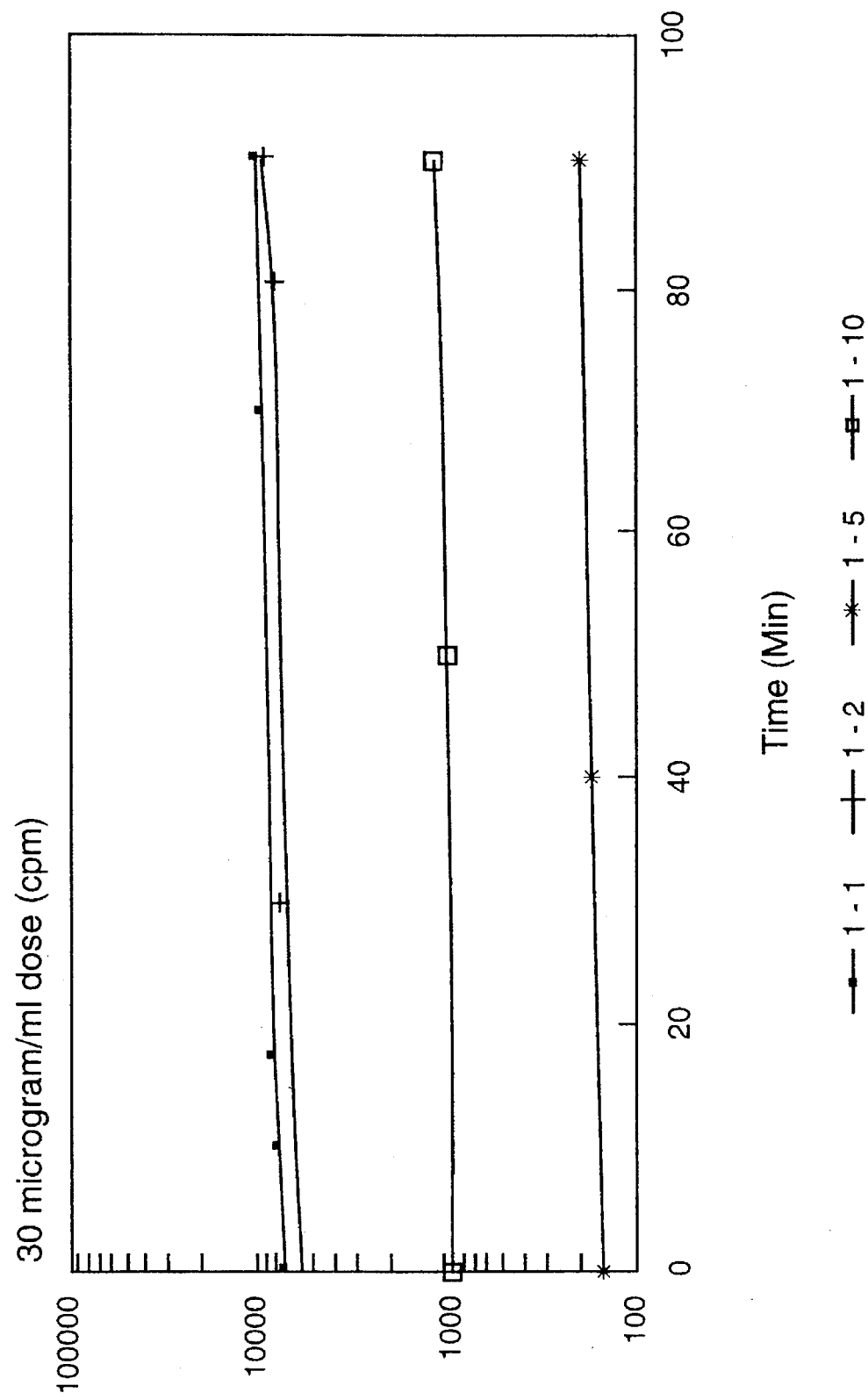
Figure 4B:
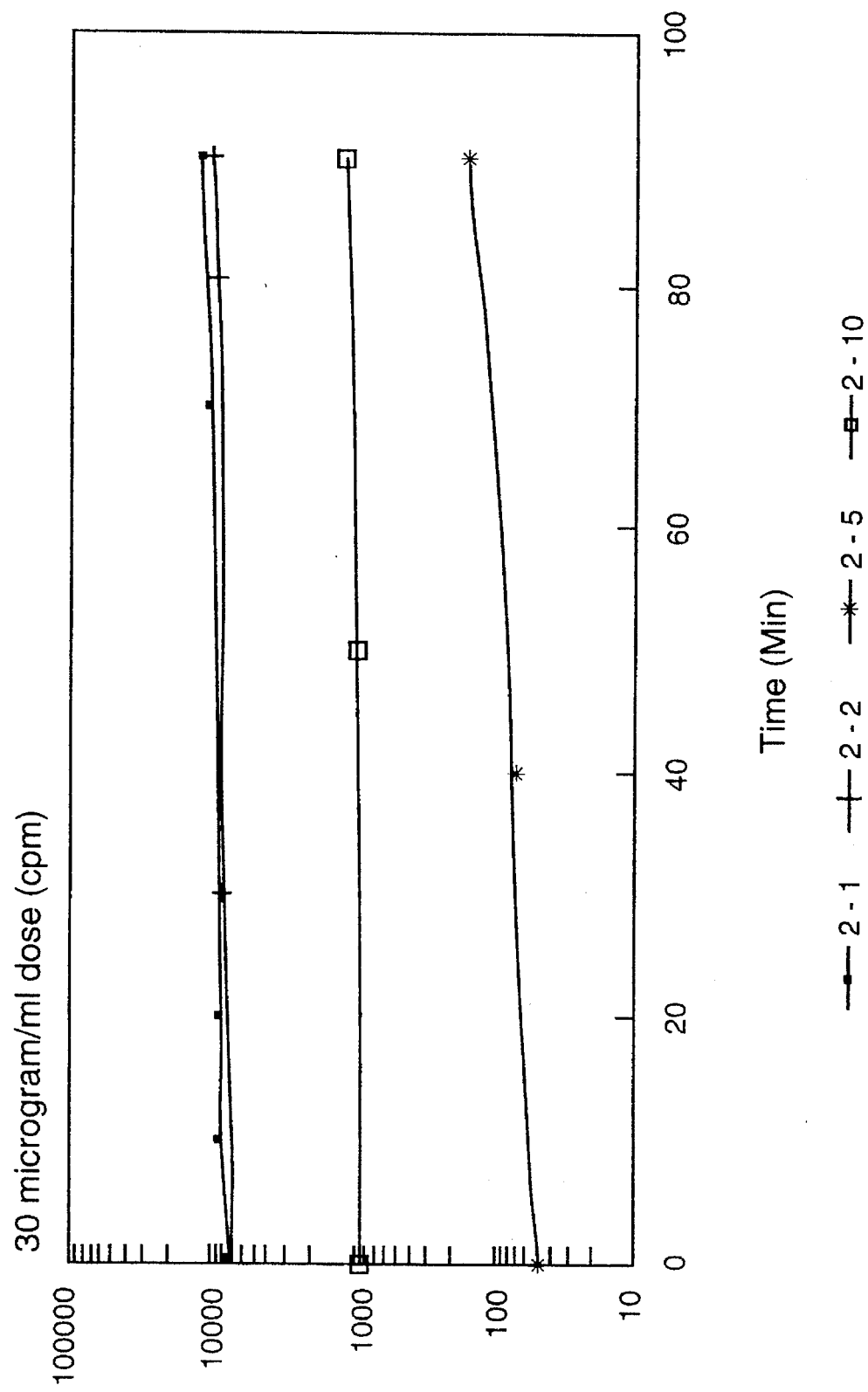
Figure 4C:
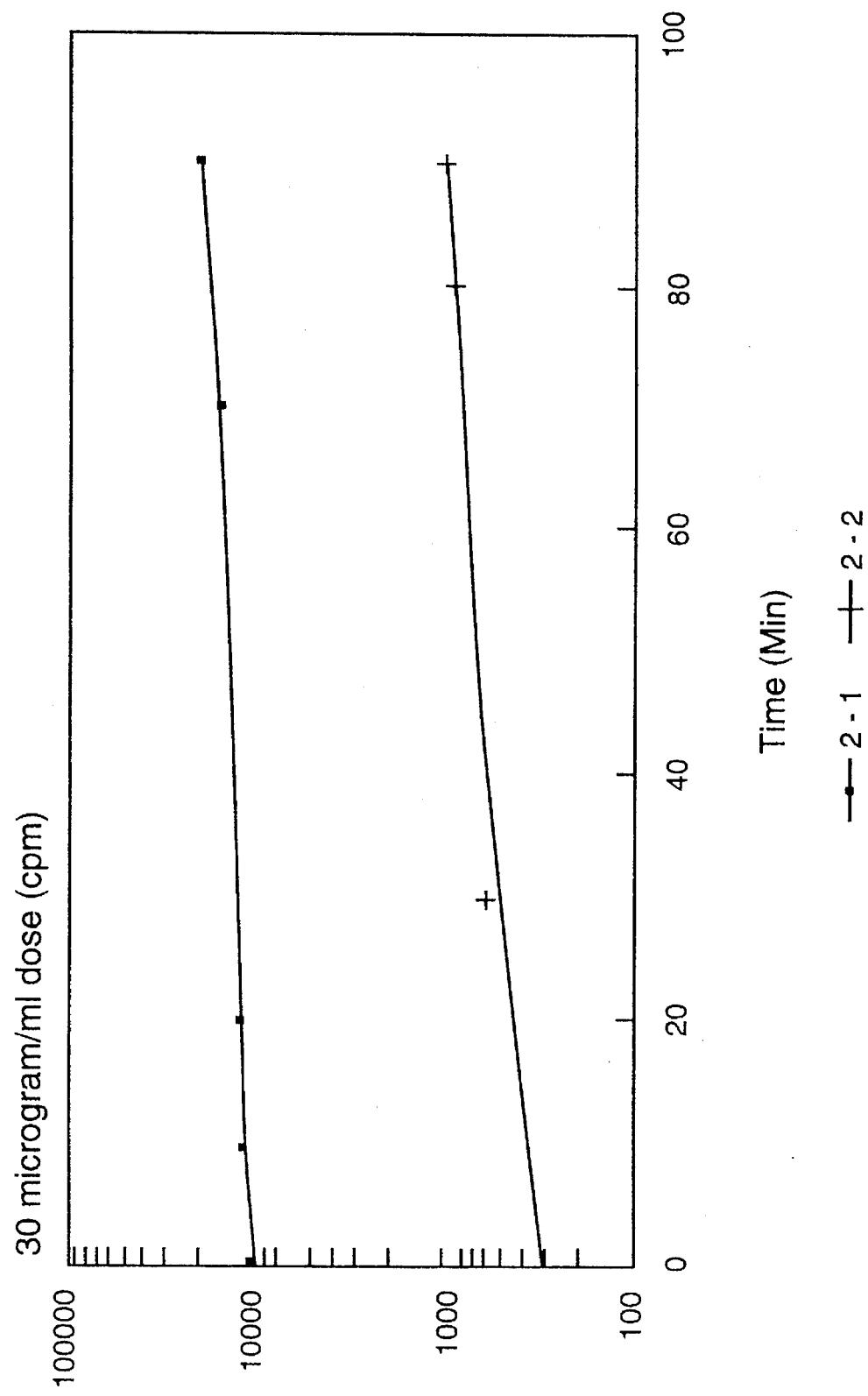

FIG. 3 is a bar graph showing half life of particles made in accordance with the present invention in blood; and FIGS. 4a–4c are plots showing in vitro biodistribution of N-RES particle agents made in accordance with the present invention, wherein different alkylene ether groups (R) are employed in the graft copolymer. FIG. 4a, R=ethylene oxide, FIG. 4b, R=ethylene oxide/isopropylene oxide, FIG. 4c, R=methylene oxide.

DETAILED DESCRIPTION OF A PREFERRED EMBODIMENT OF THE INVENTION

As mentioned supra, the overall process of the present invention involves coating an inorganic core particle with a poly (acrylic acid)-poly (alkylene ether) graft copolymer.

The inorganic core particles may be produced by any of several conventional methods. In accordance with one preferred method, the inorganic core particles are prepared by contacting aqueous solutions of an inorganic salt and an inorganic base across a porous membrane wherein the membrane contains a plurality of pores which allows the precipitation of substantially monodispersed size inorganic oxide particles on one side of the membrane and precipitation of a salt of the corresponding base on the other side of the membrane, i.e. in accordance with the teachings of co-pending U.S. application Ser. No. 07/894,260, assigned to the common assignee the subject applications. Alternatively, in accordance with another preferred embodiment, the inorganic core particles may be prepared by combining an aqueous slurry of a mettallocene with an aqueous slurry of a metal hydroxide, and milling the combined slurries to form a slurry of magnetic particles in accordance with U.S. Pat. No. 3,071,076 to Chagnon et al.

Following preparation of the inorganic core particles, the particles are then coated with a poly (acrylic acid) poly (alkylene ether) graft copolymer by adding the graft copolymer material to an aqueous solution of the particles, and subjecting the resulting aqueous mixture to sonification. The graft polymer is seen to bind by adsorption of the carboxyl moiety on or by ionic complexion of the carboxyl moiety with the surface of the inorganic particles to form a monolayer covering the particles.

In a preferred embodiment, the poly(acrylic acid)—poly-(alkylene ether) graft copolymer is made in accordance with Example I, wherein the graft copolymer is believed to have the following structure:

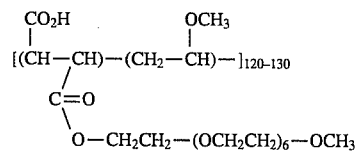

in addition to some unreacted maleic anhydride repeating units. The resulting aqueous dispersion is permitted to settle, excess fluid decanted, and the solid coated particles collected. The solid coated particles may then be purified by liquid chromatography to yield inorganic core particles evenly coated with the above graft copolymer.

The overall process will be described in greater detail:

Preparation A

Following the teachings of our co-pending application, Ser. No. 07/894,260, sub 100A ferrites are prepared by the co-precipitation of metal (+2) and metal (+3) in aqueous solutions with aqueous base across a porous or dialysis membrane. The metal salt solutions are put into a dialysis bag and the bag is sealed. The bag containing the metal salt solution is then immersed in an aqueous solution of base (i.e. ammonium hydroxide) over a period of several minutes to several days, depending on the interactions of the various reactants, and a precipitate of metal oxide forms inside of the dialysis bag. The size of the particles thus prepared is controlled by: concentration of the metal salt solutions; concentration of the base solution; pore size of the membrane; temperature of the various solutions; ionic strengths (or ionization constant) of solutions;and the contact times of each solution across the dialysis membrane, Metal oxide particles of various controlled size also can be formed by contacting an aqueous solution of metal salts with a dialysis bag filled with aqueous base. In such case, the desired metal oxide product will form outside of the dialysis bag.

Preferably, the inorganic base and the inorganic salt solutions are maintained in large volume chambers separated by a porous membrane. Accordingly, large amounts of inorganic oxide particles can be produced.

Figure 1:
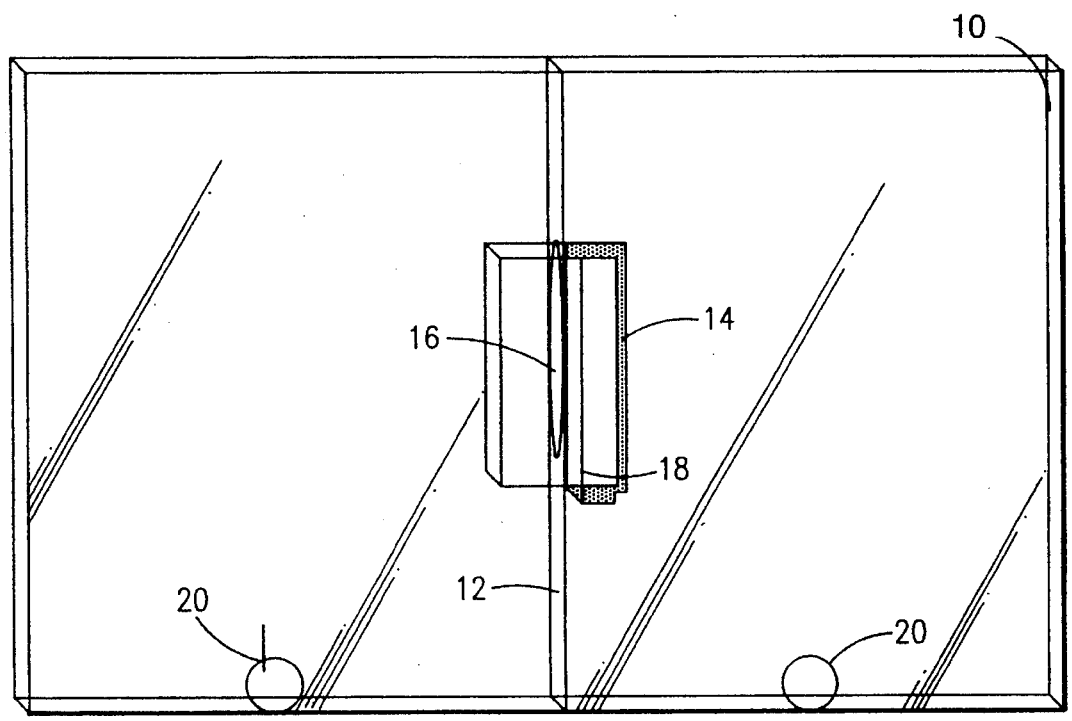
FIG. 1 is a side elevational view, in cross section, of a precipitation chamber useful for producing controlled size inorganic core particles useful in the preparation of N-RES particles in accordance with the present invention.
Figure 2A:
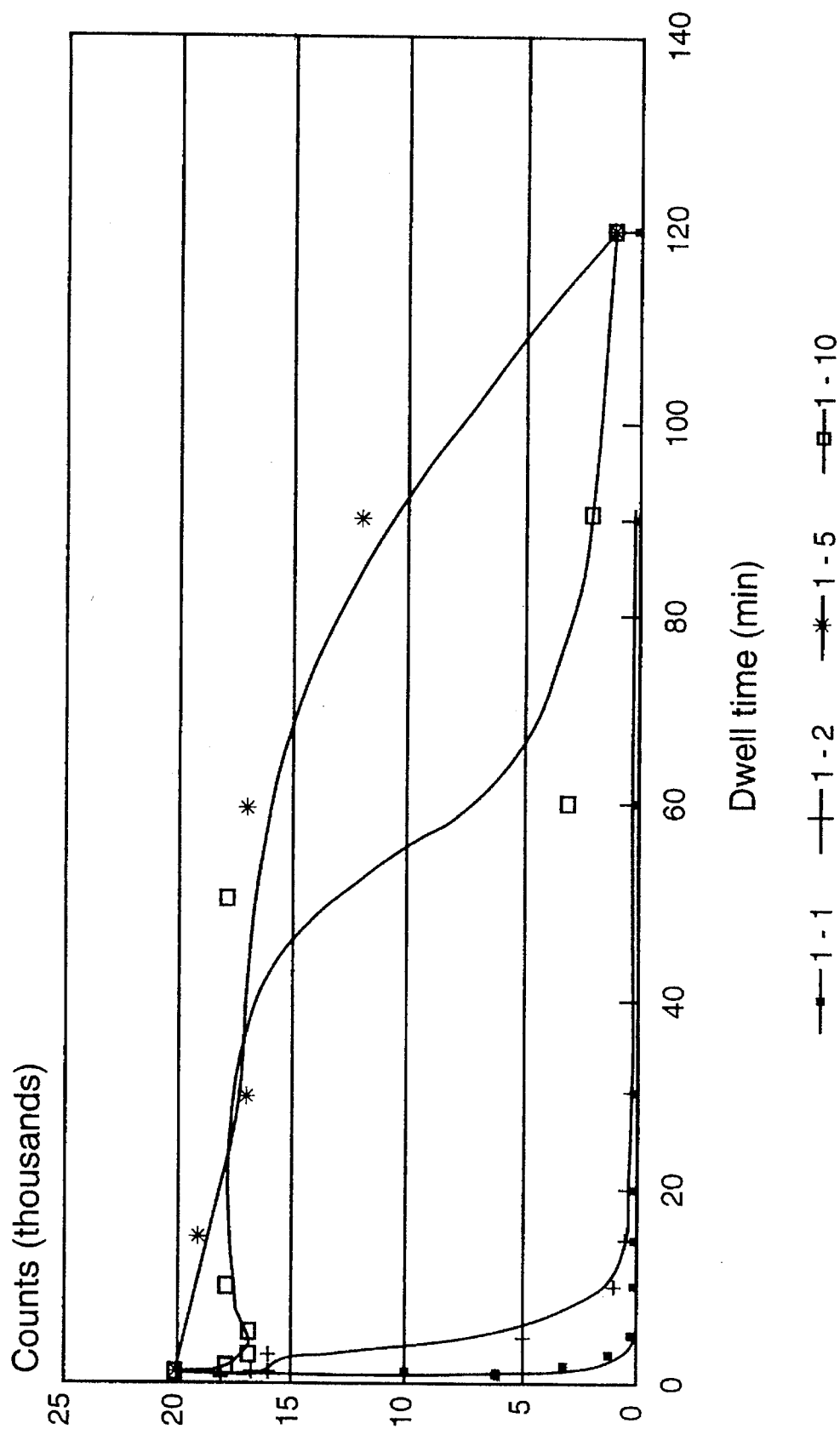
FIGS. 2a–2c are plots showing blood clearance rates for N-RES particles made in accordance with the present invention.
Figure 2B:
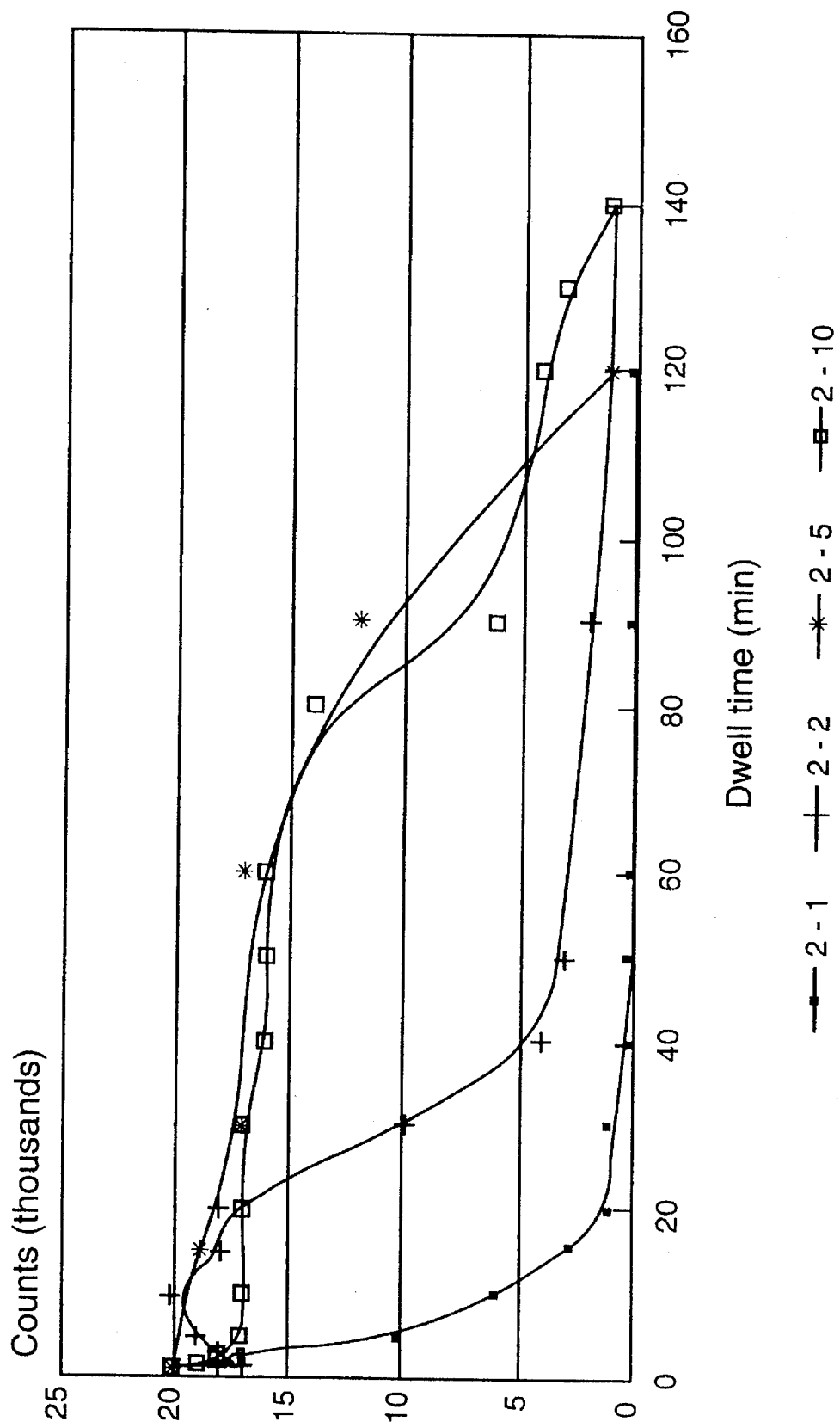
Figure 2C:
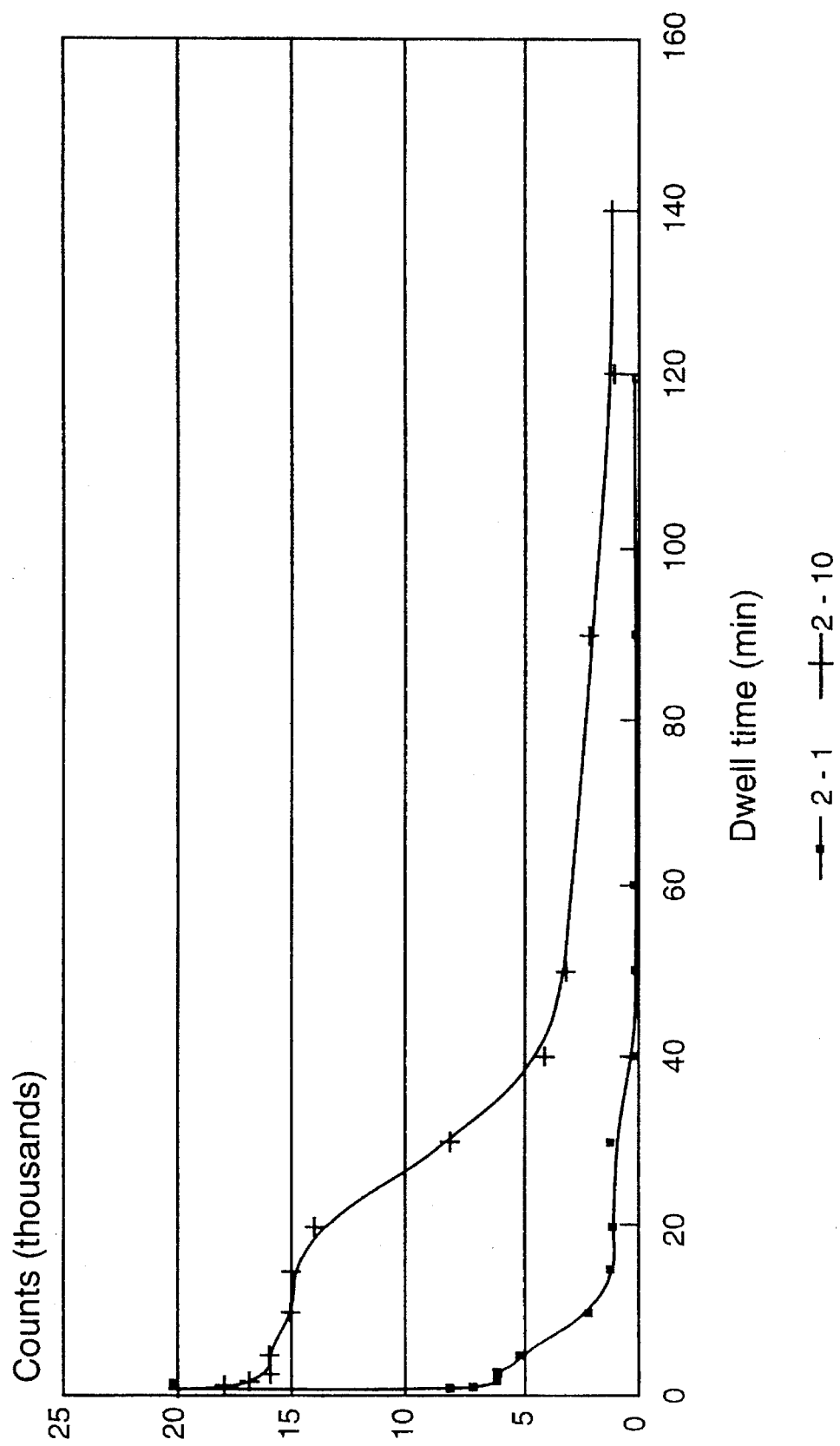

Referring to FIG. 1, a large volume chamber (10) contains a partition (12), a semi-permeable membrane (14), an opening (16), a support (18) for mounting of the membrane, and portals (20) for draining. The metal salt solution is placed on the membrane side of the chamber, such that the metal oxide particles precipitate on that side of the large volume chamber.

As noted in our aforesaid application Ser. No. 07/894,260, the size of the cationic moiety on the base side of the membrane controls the size of the precipitated inorganic oxide particle so produced near the surface of the membrane within the inorganic salt solution.. The larger the cationic moiety the slower the dissociation to cationic and anionic component. When the dissociation is relatively slow, a relatively low concentration of anionic moiety is present, providing a relatively low concentration of anion diffusing across the porous membrane and into the inorganic salt solution. Accordingly, the cationic component (of the inorganic salt) exists in large excess, thereby surrounding the slowly diffusing anion, resulting in precipitation of many small-sized inorganic oxide particles.

By contrast, if the cationic moiety of the inorganic base is relatively small, the speed of dissociation is relatively fast, providing a relatively large concentration of anionic moiety diffusing across the porous membrane and into the inorganic salt solution. At the surface of the membrane within the inorganic salt solution the cationic component (of the inorganic salt) once again exists in large excess. Accordingly, while the cationic component surrounds those anionic moieties which have diffused across the membrane, the elevated concentration of diffusing anionic moiety rapidly finds its way to the cationic surface of such a growing particle, so that a further layer of ionic bonding can result, thereby producing larger overall particle size prior to precipitation from solution.

It has been found, for example, that KOH in contact with an aqueous solution of $FeCl_2/FeCl_3$ affords iron oxide particles (($Fe_3O_4$) that are smaller in size as compared to iron oxide particles produced when LiOH is employed as the inorganic base. This would comport with the above insofar as the K+ ion is known to be relatively larger than the Li+ ion.

With respect to the foregoing, $NH_4OH$, KOH, LiOH, NaOH and other hydroxides formed by elements in group Ia of the periodic table serve as suitable inorganic base compounds. Inorganic salt solutions based on mixtures of the type $M^{(+3)}Y/M^{(+2)}Y$ include those wherein Y is selected from the group consisting of Cl, Br, I, $SO_4$, $NO_3$ and $PO_4$. M can be selected from the group consisting of Fe, Co, Ni, Zn, Mn, Mg, Ca, Ba, Sr, Cd, Hg, Al, B, Sc, Ga, V and In. The preferred inorganic salts are those which are readily productive in an aqueous medium of an anion and a cation which can combine with the aforementioned diffusing hydroxide anion to form an inorganic oxide.

Accordingly, inorganic oxide particles of the formula $M_3O_4$, $MO_1$, $MO_2$, $MO_3$, $M_2O_3$ are prepared wherein M is selected from the group consisting of Fe, Co, Ni, Zn, Mn, Hg, Ca, Ba, Sr, Cd, Hg, Al, B, Sc, Ga, V and In and mixtures thereof. It will also be appreciated that for a given metal oxide particle, the metal (M) may often be a combination of different oxidation states of the same metal component. For example, and in the preferred embodiments, $Fe_3O_4$ particles are prepared and represent a mixed Fe(+2)Fe(+3) oxide of the formula $[Fe(+2)][Fe(+3)]_2O_4$.

Alternatively, the inorganic core particles may be prepared from metallocenes following the teachings of my aforesaid U.S. Pat. No. 5,071,076. The overall process is as follows:

An aqueous metallocene slurry prepared in accordance with the teachings of our aforesaid U.S. Pat. No. 5,071,076, is combined with a second aqueous slurry of a metal hydroxide. The choice of metal hydroxide will depend upon the properties of the particles which are desired. For example, to produce magnetite particles, iron (II) hydroxide (ferrous hydroxide) is used. Other metal hydroxide which can be used to produce magnetic particles, for example, include cobalt (II) hydroxide, cobalt (III) hydroxide, iron (III) hydroxide and nickel hydroxide. Slurries of these metal hydroxides can be prepared, for example, by precipitating a salt of the metal (e.g. chloride or sulfate salt) in an aqueous medium using a base, such as sodium hydroxide or ammonium hydroxide. An aqueous iron (II) hydroxide slurry can be prepared, for example, by precipitating an aqueous solution of ferrous chloride or ferrous sulfate with ammonium or sodium hydroxide to form ferrous hydroxide (FeO(OH)). The resulting gelatinous precipitate of iron (II) hydroxide is filtered, and the solid material is collected, combined with water and milled in a high energy mill to form the slurry. The metal hydroxide slurry can contain, for example, from about 0.1 to about 40 percent (%) by weight of the metal hydroxide, preferably about 10–20% by weight.

The two slurries are combined and the mixture is milled, for example in a high energy mill, such as a commercial ball or sand mill, for a period of time sufficient to form fine magnetic particles, generally for about 1 hour to about 60 hours.

The inorganic core particle prepared by Preparation A or Preparation B is then coated with a poly(acrylic acid)-poly(alkylene ether) graft polymer to substantially uniformly coat the inorganic core particles with a monolayer of the graft polymer material. The overall process is to add to an aqueous solution of the controlled size inorganic core particles from Preparation A or Preparation B, a slight excess (10–20 percent excess) based on monolayer coverage, of the poly(acrylic) acid-poly(alkylene ether) graft polymer, and subject the resulting aqueous mixture to sonification, for 3–5 minutes, preferably about 5 minutes. The graft polymer is seen to absorb to the inorganic core particles to form a uniform monolayer covering the inorganic core particles. (As noted above, and without being held to a particular theory of absorbtion, it can be appreciated, given the structure of the inorganic core and the graft copolymer, that ionic complexation occurs, which contemplates both van der Woaals type attraction, dipole-dipole attraction, or possibly, hydrogen bonding.)

The resulting aqueous dispersion is permitted to settle, excess fluid decanted, and the solid products collected. The solid products recovered are then purified by liquid chromatography to yield controlled size inorganic core particles uniformly coated with a graph copolymer which are characterized by significantly lower RES recognition and corresponding increase in blood circulation time as compared to the uncoated inorganic core particles. The resulting "N-RES" particles thus provide enhanced RES avoidance which in turn makes the coated particles particularly useful as drug delivery vehicles and/or MRI contrast agents.

The invention will be further illustrated by the following examples:

EXAMPLE I

Step A. Preparation of Mag A($Fe_xO_y$ at $[1]^{FeII}:[2]^{FeIII}$

Combine 12.5 g. $FeCl_2 \cdot 4H_2O$ (aldrich #22029-9) and 20.0 $FeCl_3$ (Aldrich #15774-0) in 1 liter deionized $H_2O$.

Stir until solution is clear.

Precipitate with 70 ml $Nh_4OH$ (Ashland Chemicals), adding base in a slow steady stream with constant stirring, continue to stir 2–3 minutes after addition.

Place beaker on magnet for separation and decant supernatant for five washes, re-suspending in approximately 1 liter of deionized $H_2O$ after each wash.

Preparation of Poly(acrylic acid)—Polyalkylene Ether Graft Copolymer

A mixture of 10.0 grams Gantrez AN-119 (20000 mw) (ISP Technologies Inc.) and 50 ml polyethylene glycol mono-methyl ether (350 mw) was stirred at 150° C. under nitrogen for 2.5 hours. The dark solution was poured into 500 ml of toluene, and 500 ml of hexane was added to precipitate the polymeric product. After triturating the crude product with 100 ml of 1.1 toluene/hexane and decanting the solvents, the polymer was stirred in 200 ml of water at 80° C. for 5 minutes to hydrolyse the remaining anhydride groups. After cooling, the solution was filtered through a glass pad and most of the water was removed under vacuum. The residue was dissolved in 200 ml of acetone, dried with anhydrous sodium sulfate, filtered, and the solution evaporated to approximately 50 ml. This was added to 300 ml of toluene, the precipitated product rinsed with a small amount of pentane, and vacuum dried to a sticky resin, yield, 20.1 grams.

EXAMPLE II

Step A. Preparation of MagD($Fe_xO_y$ at $[1]^{FeII}:[1-45]^{FeIII}$

Combine 12.5 g $FeCl_2 \cdot 4H_2O$ (aldrich #22029-9) and 14.79 g $FeCl_3$ (Aldrich #15774-0) in a 1 liter deionized $H_2O$.

Stir until solution is clear

Precipitate with 39.0 ml $NH_4OH$ (Ashland Chemicals), adding base in a slow, steady stream with constant stirring. Continue to stir 2–3 minutes after addition.

Place beaker on magnet for separation and decant supernatant for three washes, resuspending in approximately 1 liter of deionized $H_2O$ after each wash.

Coating Procedure

N-RES coating material and iron oxide particulate were combined in a 1:1 ratio (wt/wt) and mixed by hand for several minutes. Material was then placed in a beaker in an ice bath and exposed to a strong ultrasonic field for three minutes at Intensity 6. (Model 450, Branson Ultrasonics Corp., Danbury, Conn.). After sonication, excess coating was removed by magnetic separation with re-suspension in water 2×. Sonication was repeated at Intensity 3 for three minutes. Large particle agglomerates were removed by centrifugation in 15 ml tubes in a table top centrifuge for one hour at room temperature. The suspended material was collected and pelleted material discarded.

EXAMPLE III

Step A. Metal oxides were prepared by the controlled hydrolyses of metal alkoxides in water. Oxides of single of multiple metal crystals can be thus prepared—10 grams of Iron triisopropoxide were dissolved in 100 ml of dry isopropyl alcohol. The isopropoxide solution was added dropwise to a beaker containing 1000 ml of room temperature $H_2O$. Upon contacting the water, the alkoxide immediately precipitated to form FeO. The FeO was collected by centrifugation and the alcohol water mixture discarded.

The FeO pellet was re-suspended in water by first physically shaking the pellet by exposure to an ultrasonic wave (Branson) at a setting of 9 for a period of 15 seconds.

The FeO was recollected by centrifugation and the entire re-suspension procedure was repeated three times to wash the particle.

After the final dispersion, the FeO suspension was diluted with water to a final concentration of 10 mgFe/ml solution and saved for use in coupling experiments.

EXAMPLE IV

The process of Example III was repeated, substituting for the Iron triisopropoxide $Ti(OI_p)_4$ to form $TiO2$ particles. The $TiO2$ particles were selected and coated with the graph copolymer following the procedure of Example III.

EXAMPLE V

The process of Example III was repeated, substituting for the Iron triisopropoxide $Mn(OI_p)_2$ to form $MnO2$ particles. The $MnO2$ particles were selected and coated with the graph copolymer following the procedure of Example III.

EXAMPLE VI

The process of Example III was repeated, substituting for the Iron triisopropoxide $Zn(OI_p)_2$ to form ZnO particles. The ZnO particles were selected and coated with the graph copolymer following the procedure of Example III.

Coated particles made in accordance with the present invention employed in vivo evaluation to determine blood clearance rates and biodistribution by suspending the particles in 1× PBS and 5% glucose, and injected into Long Evans Rats from Charles River Laboratories (290–300 kilogram) at a rate of 2 milligrams Fe/Kg bodyweight. Each animal was injected with 500 microliters of solution and 100 microliter blood samples drawn at 1, 10, 20, 30, 60, 90, 120 and 180 minutes.

The animals were then sacrificed and organs analyzed for biodistribution of material. Blood samples and organs were measured using an Autogamma Sintillation Counter by Packard (Model No. 6160). Readings were obtained by reading injection material and adjusting window of maximum counts. All readings were done at this setting for one minute time periods, and the results were recorded below and plotted in FIGS. 2a–c, 3 and 4a–4c.

| R | X | Blood Pool Dwell Time (min) | Sample No. |
| --- | --- | --- | --- |
| m[$O-CH_2-CH_2$]O | 1 | 2 | 1-1 |
| m[$O-CH_2-CH_2$]O | 2 | 10 | 1-2 |
| m[$O-CH_2-CH_2$]O | 5 | 60 | 1-5 |
| m[$O-CH_2-CH_2$]O | 10 | 50 | 1-10 |

-continued

| R | X | Blood Pool Dwell Time (min) | Sample No. |
|---|---|---|---|
| (CH$_2$CH2—O—CH2—CH(CH$_3$)—CH2)O | 1 | 5 | 2-1 |
| (CH$_2$CH2—O—CH2—CH(CH$_3$)—CH2)O | 2 | 20 | 2-2 |
| (CH$_2$CH2—O—CH2—CH(CH$_3$)—CH2)O | 5 | 90 | 2-5 |
| (CH$_2$CH2—O—CH2—CH(CH$_3$)—CH2)O | 10 | 80 | 2-10 |
| O—(CH$_2$—O—CH$_2$)—O | 1 | 1 | 3-1 |
| O—(CH$_2$—O—CH$_2$)—O | 10 | 20 | 3-10 |

We claim:

1. A MRI responsive particle comprising:
   a. an inorganic core particle; and
   b. a poly(acrylic acid)-poly(alkylene ether) graft copolymer coating surrounding said core particle.

2. A coated particle according to claim 1 wherein the inorganic core particles are selected from the group consisting of a metal, metal alloy, and metal salt, metal organic particles, metal oxides, metal hydroxides and mixed lattices thereof.

3. A coated particle according to claim 2, wherein the inorganic core particle is selected from the group consisting of Fe, Fe$_3$O$_4$, Fe$_2$O$_3$, Al$_2$O$_3$, TiO$_2$, ZnO, FeO, and mixtures thereof.

4. A coated particle according to claim 1, wherein the inorganic core comprises a magnetic particle derived from the milling of a metallocene with an aqueous slurry of a metal or metal hydroxide.

5. A coated particle according to claim 1, wherein the inorganic core particle comprises a controlled size particle.

6. A core particle wherein the graft copolymer has the following structure:

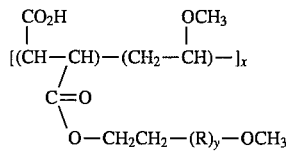

wherein R is an alkylene ether of $C_1$–$C_6$, x is a whole number of at least 1, and y is a whole number of at least 1.

7. The graft copolymer of claim 6 wherein x is a whole number from 120–130, y is a whole number from 5–10 and R is an ethylene oxide repeat unit.

8. A coated particle according to claim 6, wherein the poly(alkylene ether) comprises a alkylene ether selected from the group consisting of methylene oxide, ethylene oxide, propylene oxide, isopropylene oxide, and butylene oxide, isobutylene oxide, or mixtures thereof.

9. A method for producing MRI responsive particles comprising the steps of:
   a. combining an aqueous solution of an inorganic core particle with an aqueous solution of a poly(acrylic acid)-poly(alkylene ether) copolymer; and
   b. sonifying the resulting combination produced in step (a) for a time sufficient to substantially uniformly coat the core particles.

10. A process according to claim 8, wherein the inorganic core particles are prepared by precipitation of an aqueous solution of an inorganic salt in an inorganic base across a porous membrane.

11. A process according to claim 8, wherein the inorganic core particles are prepared by combining an aqueous slurry of a metallocene with an aqueous slurry of a metal hydroxide, and milling the combination for a period of time sufficient to form a slurry of magnetic particles.

12. A process according to claim 8, wherein the poly(acrylic acid)-poly(alkylene ether) graft copolymer is added to the inorganic core particles in an excess of 10–1000 percent (%).

13. A process according to claim 8, wherein said inorganic core particles are of a controlled size.

* * * * *